US011129684B2

(12) United States Patent
Itkowitz et al.

(10) Patent No.: US 11,129,684 B2
(45) Date of Patent: *Sep. 28, 2021

(54) SYSTEM AND METHOD FOR MAINTAINING A TOOL POSITION AND ORIENTATION

(71) Applicant: INTUITIVE SURGICAL OPERATIONS, INC., Sunnyvale, CA (US)

(72) Inventors: Brandon D. Itkowitz, San Jose, CA (US); Nitish Swarup, Sunnyvale, CA (US); Paul G. Griffiths, Santa Clara, CA (US); Goran Lynch, Oakland, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/743,218

(22) Filed: Jan. 15, 2020

(65) Prior Publication Data

US 2020/0146764 A1    May 14, 2020

Related U.S. Application Data

(63) Continuation of application No. 16/101,328, filed on Aug. 10, 2018, now Pat. No. 10,575,910, which is a
(Continued)

(51) Int. Cl.
*G01B 21/04* (2006.01)
*A61B 34/00* (2016.01)
(Continued)

(52) U.S. Cl.
CPC .......... *A61B 34/70* (2016.02); *A61B 1/00149* (2013.01); *A61B 34/30* (2016.02);
(Continued)

(58) Field of Classification Search
CPC ........... G05B 2219/36417; G05B 2219/42162; G01B 21/045; G01B 7/004; G01D 18/00;
(Continued)

(56) References Cited

U.S. PATENT DOCUMENTS 5,465,037 A    11/1995    Huissoon et al.
7,206,626 B2 *    4/2007    Quaid, III .............. A61B 34/70
                                                        600/407
(Continued)

FOREIGN PATENT DOCUMENTS

CN         101421080 A      4/2009
DE      102004010332 B3    10/2005
(Continued)

OTHER PUBLICATIONS

Extended European Search Report for Application No. 15765922.8, dated Oct. 18, 2017, 8 pages.
(Continued)

*Primary Examiner* — Dalena Tran
(74) *Attorney, Agent, or Firm* — Artegis Law Group, LLP

(57) ABSTRACT

A system and method of maintaining a tool position and orientation for a computer-assisted device include an articulated structure including a plurality of joints and a control unit coupled to the articulated structure. The control unit is configured to determine whether a cannula or an instrument is coupled to a distal end of the articulated structure and in response to determining that the cannula or the instrument is coupled to the distal end of the articulated structure: determine an initial position and orientation of the instrument prior to detection of a disturbance in a first joint of the plurality of joints; determine, during the disturbance in the first joint, a current position and orientation of the instrument; determine a difference between the current position and orientation and the initial position and orientation; and
(Continued)

drive at least a second joint of the plurality of joints based on the difference.

20 Claims, 4 Drawing Sheets

Related U.S. Application Data continuation of application No. 15/125,533, filed as application No. PCT/US2015/021089 on Mar. 17, 2015, now Pat. No. 10,070,931.

(60) Provisional application No. 62/024,887, filed on Jul. 15, 2014, provisional application No. 61/954,261, filed on Mar. 17, 2014.

(51) Int. Cl.
   *A61B 34/30* (2016.01)
   *A61B 1/00* (2006.01)
   *B25J 9/16* (2006.01)
   *A61B 17/00* (2006.01)
   *A61B 34/20* (2016.01)

(52) U.S. Cl.
   CPC .......... *B25J 9/1607* (2013.01); *B25J 9/1633* (2013.01); *A61B 2017/00017* (2013.01); *A61B 2034/2059* (2016.02); *A61B 2034/301* (2016.02); *A61B 2034/304* (2016.02); *A61B 2034/305* (2016.02)

(58) Field of Classification Search
   CPC ....... Y10S 901/02; A61B 34/30; A61B 34/37; A61B 34/70; A61B 2017/00017; A61B 90/50; B25J 9/06; B25J 9/1607; B25J 9/1664; B25J 9/1682
   USPC ............... 700/245, 251, 248, 252, 262, 263; 600/417, 424; 901/6, 30
   See application file for complete search history.

(56) References Cited

U.S. PATENT DOCUMENTS

| | | | |
|---|---|---|---|
| 7,763,015 B2 | 7/2010 | Cooper et al. | |
| 7,819,859 B2 | 10/2010 | Prisco et al. | |
| 7,837,674 B2 | 11/2010 | Cooper | |
| 8,004,229 B2 | 8/2011 | Nowlin et al. | |
| 8,271,130 B2 | 9/2012 | Hourtash et al. | |
| 8,343,171 B2 * | 1/2013 | Farritor | A61B 34/30 |
| | | | 606/130 |
| 8,400,094 B2 | 3/2013 | Schena | |
| 8,541,970 B2 | 9/2013 | Nowlin et al. | |
| 8,620,473 B2 | 12/2013 | Diolaiti et al. | |
| 8,624,537 B2 | 1/2014 | Nowlin et al. | |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 8,918,211 B2 | 12/2014 | Diolaiti et al. | |
| 9,078,686 B2 | 7/2015 | Schena | |
| 9,084,623 B2 | 7/2015 | Gomez et al. | |
| 9,107,683 B2 | 8/2015 | Houtash et al. | |
| 9,138,129 B2 | 9/2015 | Diolaiti | |
| 9,296,104 B2 | 3/2016 | Swarup et al. | |
| 9,333,042 B2 | 5/2016 | Diolaiti et al. | |
| 9,345,544 B2 | 5/2016 | Hourtash et al. | |
| 9,375,284 B2 | 6/2016 | Hourtash | |
| 9,415,510 B2 | 8/2016 | Hourtash et al. | |
| 9,468,501 B2 | 10/2016 | Hourtash et al. | |
| 9,469,034 B2 | 10/2016 | Diolaiti et al. | |
| 9,492,235 B2 | 11/2016 | Hourtash et al. | |
| 9,492,927 B2 | 11/2016 | Diolaiti et al. | |
| 9,526,581 B2 | 12/2016 | Bodduluri et al. | |
| 9,603,666 B2 * | 3/2017 | Elhawary | A61B 1/00163 |
| 9,710,921 B2 | 7/2017 | Wong et al. | |
| 9,770,305 B2 * | 9/2017 | Farritor | A61B 34/30 |
| 10,064,689 B2 | 9/2018 | Swarup et al. | |
| 10,070,931 B2 | 9/2018 | Itkowitz et al. | |
| 10,575,910 B2 | 3/2020 | Itkowitz et al. | |
| 10,610,316 B2 | 4/2020 | Swarup et al. | |
| 2003/0021107 A1 | 1/2003 | Howell et al. | |
| 2003/0025473 A1 | 2/2003 | Nagata et al. | |
| 2006/0025668 A1 | 2/2006 | Peterson et al. | |
| 2009/0048611 A1 | 2/2009 | Funda et al. | |
| 2009/0192524 A1 | 7/2009 | Itkowitz et al. | |
| 2009/0326318 A1 | 12/2009 | Tognaccini et al. | |
| 2010/0138183 A1 | 6/2010 | Jensen et al. | |
| 2010/0204713 A1 | 8/2010 | Ruiz | |
| 2011/0054303 A1 | 3/2011 | Barrick et al. | |
| 2011/0238082 A1 | 9/2011 | Wenderow et al. | |
| 2013/0085510 A1 | 4/2013 | Stefanchik et al. | |
| 2013/0096576 A1 | 4/2013 | Cooper et al. | |
| 2014/0031983 A1 | 1/2014 | Low et al. | |
| 2014/0039681 A1 | 2/2014 | Bowling et al. | |
| 2014/0052153 A1 | 2/2014 | Griffiths et al. | |
| 2014/0052154 A1 | 2/2014 | Griffiths et al. | |
| 2014/0236175 A1 | 8/2014 | Cooper et al. | |
| 2014/0305995 A1 | 10/2014 | Shelton, IV et al. | |
| 2014/0316430 A1 | 10/2014 | Hourtash et al. | |
| 2014/0358161 A1 | 12/2014 | Hourtash et al. | |
| 2015/0032126 A1 | 1/2015 | Nowlin et al. | |
| 2015/0051733 A1 | 2/2015 | Nowlin et al. | |
| 2015/0150639 A1 | 6/2015 | Diolaiti et al. | |
| 2016/0030124 A1 | 2/2016 | Kishi et al. | |
| 2018/0338808 A1 | 11/2018 | Swarup et al. | |
| 2018/0344417 A1 | 12/2018 | Itkowitz et al. | |
| 2019/0117313 A1 | 4/2019 | Crawford | |

FOREIGN PATENT DOCUMENTS

| | | |
|---|---|---|
| DE | 102008041602 A1 | 3/2010 |
| EP | 0571827 A1 | 12/1993 |
| EP | 1234641 A1 | 8/2002 |
| EP | 1642690 A2 | 4/2006 |
| JP | H0699372 A | 4/1994 |
| JP | 2011206312 A | 10/2011 |
| WO | WO-2006079108 A1 | 7/2006 |
| WO | WO-2006124390 A2 | 11/2006 |
| WO | WO-2011143023 A1 | 11/2011 |
| WO | WO-2011143024 A1 | 11/2011 |
| WO | WO-2012158458 A2 | 11/2012 |
| WO | WO-2013048957 A1 | 4/2013 |
| WO | WO-2013181503 A1 | 12/2013 |
| WO | WO-2013181507 A1 | 12/2013 |
| WO | WO-2013181516 A1 | 12/2013 |
| WO | WO-2014028702 A1 | 2/2014 |
| WO | WO-2014028703 A1 | 2/2014 |
| WO | WO-2014146095 A1 | 9/2014 |
| WO | WO-2014146107 A1 | 9/2014 |
| WO | WO-2014146113 A1 | 9/2014 |
| WO | WO-2014146119 A1 | 9/2014 |
| WO | WO-2014146120 A1 | 9/2014 |
| WO | WO-2015142798 A1 | 9/2015 |
| WO | WO-2015142947 A1 | 9/2015 |

OTHER PUBLICATIONS

Extended European Search Report for Application No. EP15765353.6, dated Nov. 13, 2017, 9 pages.

International Search Report and Written Opinion for Application No. PCT/US15/21089, dated Jun. 19, 2015, 10 pages.

International Search Report and Written Opinion for Application No. PCT/US15/21097, dated Jul. 1, 2015, 16 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(56) References Cited

OTHER PUBLICATIONS

Extended European Search Report for Application No. EP21166255.6 dated Jul. 20, 2021, 10 pages.

* cited by examiner

SYSTEM AND METHOD FOR MAINTAINING A TOOL POSITION AND ORIENTATION

RELATED APPLICATIONS

The present application is continuation of U.S. patent application Ser. No. 16/101,328 entitled "System and Method for Maintaining a Tool Position and Orientation" filed Aug. 10, 2018, which is continuation of U.S. patent application Ser. No. 15/125,533 entitled "System and Method for Maintaining a Tool Pose" filed Sep. 12, 2016 and now U.S. Pat. No. 10,070,931, which is the U.S. national phase of International Application No. PCT/US2015/021089 entitled "System and Method for Maintaining a Tool Pose" filed Mar. 17, 2015, which designated the U.S. and claims priority to U.S. Provisional Patent Application No. 62/024,887 entitled "System and Method for Aligning with a Reference Target" filed Jul. 15, 2014 and U.S. Provisional Patent Application No. 61/954,261 entitled "System and Method for Aligning with a Reference Target" filed Mar. 17, 2014, the entire contents of each of which are incorporated herein by reference.

The present disclosure is also related to U.S. Provisional Patent Application No. 62/134,207 entitled "System and Method for Integrated Operating Table," filed Mar. 17, 2015, U.S. Provisional Patent Application No. 62/134,212 entitled "System and Method for Reducing Tool Disturbances" and filed Mar. 17, 2015, and PCT Patent Application No. PCT/US15/21097 entitled "System and Method for Aligning with a Reference Target" and filed Mar. 17, 2015, the entire contents of each of which are incorporated herein by reference.

TECHNICAL FIELD

The present disclosure relates generally to operation of devices with articulated arms and more particularly to maintaining a tool pose.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semiautonomous motion of one or more articulated arms and/or end effectors. These one or more articulated arms and/or end effectors each include a combination of links and articulated joints that support motion of the articulated arms and/or end effectors. In many cases, the articulated joints are manipulated to obtain a desired position and/or orientation (collectively, a desired pose) of a corresponding tool located at a distal end of the links and articulated joints of a corresponding articulated arm and/or end effector. Each of the articulated joints proximal to the tool provides the corresponding articulated arm and/or end effector with at least one degree of freedom that may be used to manipulate the position and/or orientation of the corresponding tool. In many cases, the corresponding articulated arms and/or end effectors may include at least six degrees of freedom that allow for controlling a x, y, and z position of the corresponding tool as well as a roll, pitch, and yaw orientation of the corresponding tool. To provide for greater flexibility in control of the pose of the corresponding tool, the corresponding articulated arms and/or end effectors are often designed to include redundant degrees of freedom. When redundant degrees of freedom are present it is possible that multiple different combinations of positions and/or orientations of the articulated joints may be used to obtain the same pose of the corresponding tool. This creates a null space where even though the articulated joints are moving, the pose of the corresponding tool is not.

As each of the articulated arms and/or end effectors is being operated, the articulated arm and/or end effector may be subject to motion, both planned and unplanned, that may result in movement in one or more of the articulated joints. As this motion changes the positions and/or orientations of the one or more articulated joints, the changes may introduce undesirable alteration to the pose of a tool being manipulated by the articulated arm. This alteration to the pose may result in injury to a patient, injury to personnel in proximity to the articulated arms and/or end effectors, damage to the articulated arms and/or end effectors, damage to other devices in proximity to the articulated arms and/or end effectors, breach of a sterile field, and/or other undesirable outcomes.

Accordingly, it would be desirable to maintain a pose of a tool in the presence of disturbances in articulated joints located proximal to the tool.

SUMMARY

Consistent with some embodiments, a computer-assisted medical device includes an articulated arm including one or more first joints and one or more second joints, a tool distal to the one or more first joints and the one or more second joints, and a control unit coupled to the first joints and the second joints. The control unit maintains a pose of the tool during movement of the one or more first joints using the one or more second joints by determining a reference coordinate frame for the tool, determining a reference transform of the tool in the reference coordinate frame prior to the movement of the one or more first joints, determining an actual transform of the tool in the reference coordinate frame while the one or more first joints are being moved, determining differences between the reference transform and the actual transform, and maintaining the pose of the tool by driving the second joints based on the differences.

Consistent with some embodiments, a method of compensating for motion in an articulated arm of a computer-assisted medical device includes determining a pose of a tool of the medical device and maintaining the pose of the tool during movement of one or more first joints of an articulated arm proximal to the tool using one or more second joints proximal to the tool. The pose is maintained by determining a reference coordinate frame for the tool, determining a reference transform of the tool in the reference coordinate frame prior to the movement of the one or more first joints, determining an actual transform of the tool in the reference coordinate frame while the one or more first joints are being moved, determining differences between the reference transform and the actual transform, and maintaining the pose of the tool by driving the second joints based on the differences. The pose includes a position and an orientation.

Consistent with some embodiments, a non-transitory machine-readable medium including a plurality of machine-readable instructions which when executed by one or more processors associated with a medical device are adapted to cause the one or more processors to perform a method. The method includes determining a pose of a tool of the medical device and maintaining the pose of the tool during movement of one or more first joints of an articulated arm proximal to the tool using one or more second joints proximal to the tool. The pose is maintained by determining a reference coordinate frame for the tool, determining a reference transform of the tool in the reference coordinate frame prior to the movement of the one or more first joints, determining an actual transform of the tool in the reference coordinate frame while the one or more first joints are being moved, determining differences between the reference transform and the actual transform, and maintaining the pose of the tool by driving the second joints based on the differences. The pose includes a position and an orientation.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
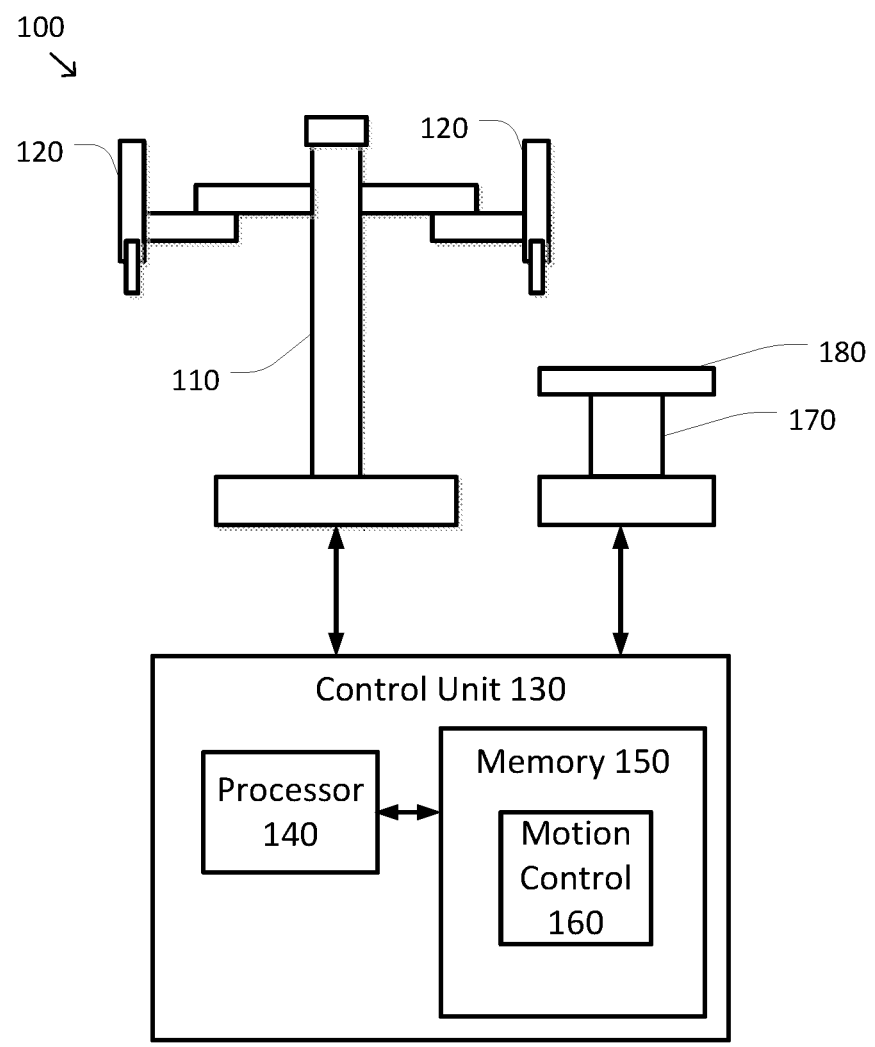
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 may support one or more end effectors. In some examples, device 110 may be consistent with a computer-assisted surgical device. The one or more articulated arms 120 may each provide support for one or more tools, surgical instruments, imaging devices, and/or the like mounted to a distal end of at least one of the articulated arms 120. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 may support articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a control pendant for controlling the position and/or orientation of table top 180. In some embodiments, surgical table 170 may correspond to one or more of the operating tables commercialized by Trumpf Medical Systems GmbH of Germany.

Surgical table 170 may also be coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may plan and/or assist in the planning of motion for surgical table 170 and/or table top 180. In some examples, motion control application 160 may prevent motion of surgical table 170 and/or table top 180, such as by preventing movement of surgical table 170 and/or table top 180 through use of the control pendant. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Figure 2:
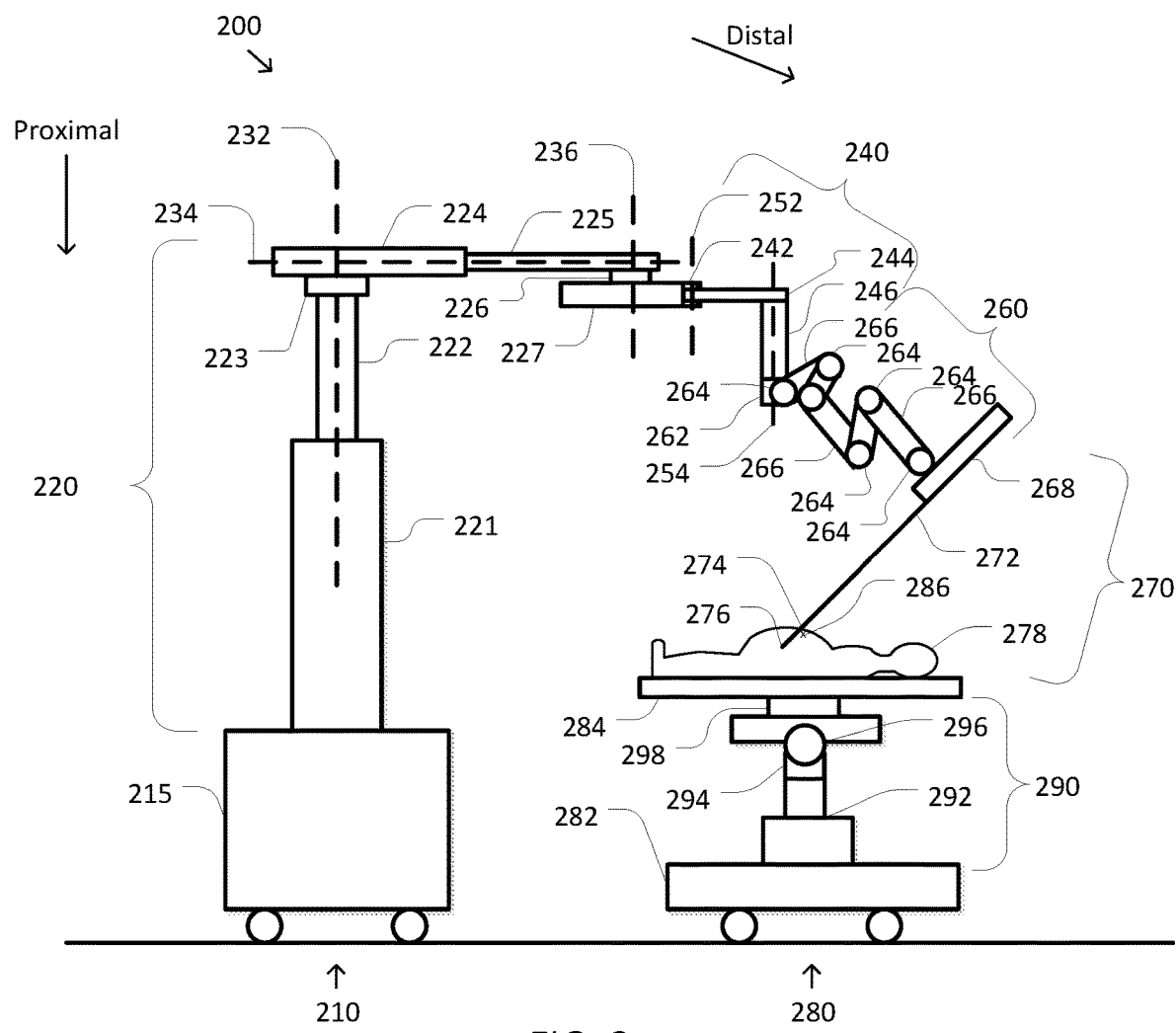
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 may be coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile or patient-side cart 215 is a set-up structure 220. Coupled to a distal end of the set-up structure is a series of set-up joints 240. And coupled to a distal end of the set-up joints 240 is a manipulator 260, such as a universal surgical manipulator. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 180. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an orientation platform 227.

The links and joints of the set-up structure 220 include various degrees of freedom for changing the position and orientation (i.e., the pose) of the orientation platform 227. For example, the two-part column may be used to adjust a height of the orientation platform 227 by moving the shoulder joint 223 up and down along an axis 232. The orientation platform 227 may additionally be rotated about the mobile cart 215, the two-part column, and the axis 232 using the shoulder joint 223. The horizontal position of the orientation platform 227 may also be adjusted along an axis 234 using the two-part boom. And the orientation of the orientation platform 227 may also adjusted by rotation about an axis 236 using the wrist joint 226. Thus, subject to the motion limits of the links and joints in the set-up structure 220, the position of the orientation platform 227 may be adjusted vertically above the mobile cart 215 using the two-part column. The positions of the orientation platform 227 may also be adjusted radially and angularly about the mobile cart 215 using the two-part boom and the shoulder joint 223, respectively. And the angular orientation of the orientation platform 227 may also be changed using the wrist joint 226.

The orientation platform 227 may be used as a mounting point for one or more articulated arms. The ability to adjust the height, horizontal position, and orientation of the orientation platform 227 about the mobile cart 215 provides a flexible set-up structure for positioning and orienting the one or more articulated arms about a work space, such as a patient, located near the mobile cart 215. FIG. 2 shows a single articulated arm coupled to the orientation platform using a first set-up or flex joint 242. And although only one articulated arm is shown, one of ordinary skill would understand that multiple articulated arms may be coupled to the orientation platform 227 using additional first set-up joints.

The first set-up joint 242 forms the most proximal portion of the set-up joints 240 section of the articulated arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the orientation platform 227 about an axis 252 using the first set-up joint 242, adjust a radial or horizontal distance between the first set-up joint 242 and the link 246, adjust a height of a manipulator mount 262 at the distal end of link 246 relative to the orientation platform along an axis 254, and rotate the manipulator mount 262 about axis 254. In some examples, the set-up joints 240 may further include additional joints, links, and axes permitting additional degrees of freedom for altering a pose of the manipulator mount 262 relative to the orientation platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument or manipulator tool 270 is mounted to the instrument carriage 268. The tool 270 includes a shaft 272, which is aligned along an insertion axis. The shaft 272 is typically aligned so that is passes through a remote center 274 associated with the manipulator 260. Location of the remote center 274 is typically maintained in a fixed translational relationship relative to the manipulator mount 262 so that operation of the joints 264 in the manipulator 260 result in rotations of the shaft 272 about the remote center 274. Depending upon the embodiment, the fixed translational relation of the remote center 274 relative to the manipulator mount 262 is maintained using physical constraints in the joints 264 and links 266 of the manipulator 260, using software constraints placed on the motions permitted for the joints 264, and/or a combination of both. In some examples, the remote center 274 may correspond to a location of a surgical port or incision site in a patient 278 after the manipulator 260 is docked with the patient 278. Because the remote center 274 corresponds to the surgical port, as the tool 270 is used, the remote center 274 remains stationary relative to the patient 278 to limit stresses on the anatomy of the patient 278 at the remote center 274. In some examples, the shaft 272 may be passed through a cannula (not shown) located at the surgical port.

At the distal end of the shaft 272 is a tool or tool tip 276. The degrees of freedom in the manipulator 260 due to the joints 264 and the links 266 may permit at least control of the roll, pitch, and yaw of the shaft 272 and/or the tool tip 276 relative to the manipulator mount 262. In some examples, the degrees of freedom in the manipulator 260 may further include the ability to advance and/or retreat the shaft 272 using the instrument carriage 268 so that the tool tip 276 may be advanced and/or retreated along the insertion axis and relative to the remote center 274. In some examples, the manipulator 260 may be consistent with a universal surgical manipulator for use with the da Vinci® Surgical System commercialized by Intuitive Surgical, Inc. of Sunnyvale, Calif. In some examples, the tool 270 may be an imaging device such as an endoscope, a gripper, a surgical tool such as a cautery or a scalpel, and/or the like. In some examples, the tool tip 276 may include additional degrees of freedom, such as roll, pitch, yaw, grip, and/or the like that allow for additional localized manipulation of portions of the tool tip 276 relative to the shaft 272.

During a surgery or other medical procedure, the patient 278 is typically located on the surgical table 280. The surgical table 280 includes a table base 282 and a table top 284 with the table base 282 being located in proximity to mobile cart 215 so that the instrument 270 and/or tool tip 276 may be manipulated by the computer-assisted device 210 while docked to the patient 278. The surgical table 280 further includes an articulated structure 290 that includes one or more joints or links between the table base 282 and the table top 284 so that the relative location of the table top 284, and thus the patient 278, relative to the table base 280 may be controlled. In some examples, the articulated structure 290 may be configured so that the table top 284 is controlled relative to a virtually-defined iso center 286 that may be located at a point above the table top 284. In some examples, iso center 286 may be located within the interior of the patient 278. In some examples, iso center 286 may be collocated with the body wall of the patient at or near one of the port sites, such as a port site corresponding to remote center 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the iso center 286. The tilt 294 allows the table top 284 to be tilted side-to-side so that either the right or left side of the patient 278 may be rotated upward relative to the other side of the patient 278 (i.e., about a longitudinal or head-to-toe axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about iso center 286. The articulated structure 290 further includes additional links and joints 298 to slide the table top 284 back and forth relative to the table base 282 with generally a left and/or right motion as depicted in FIG. 2.

Figure 3:
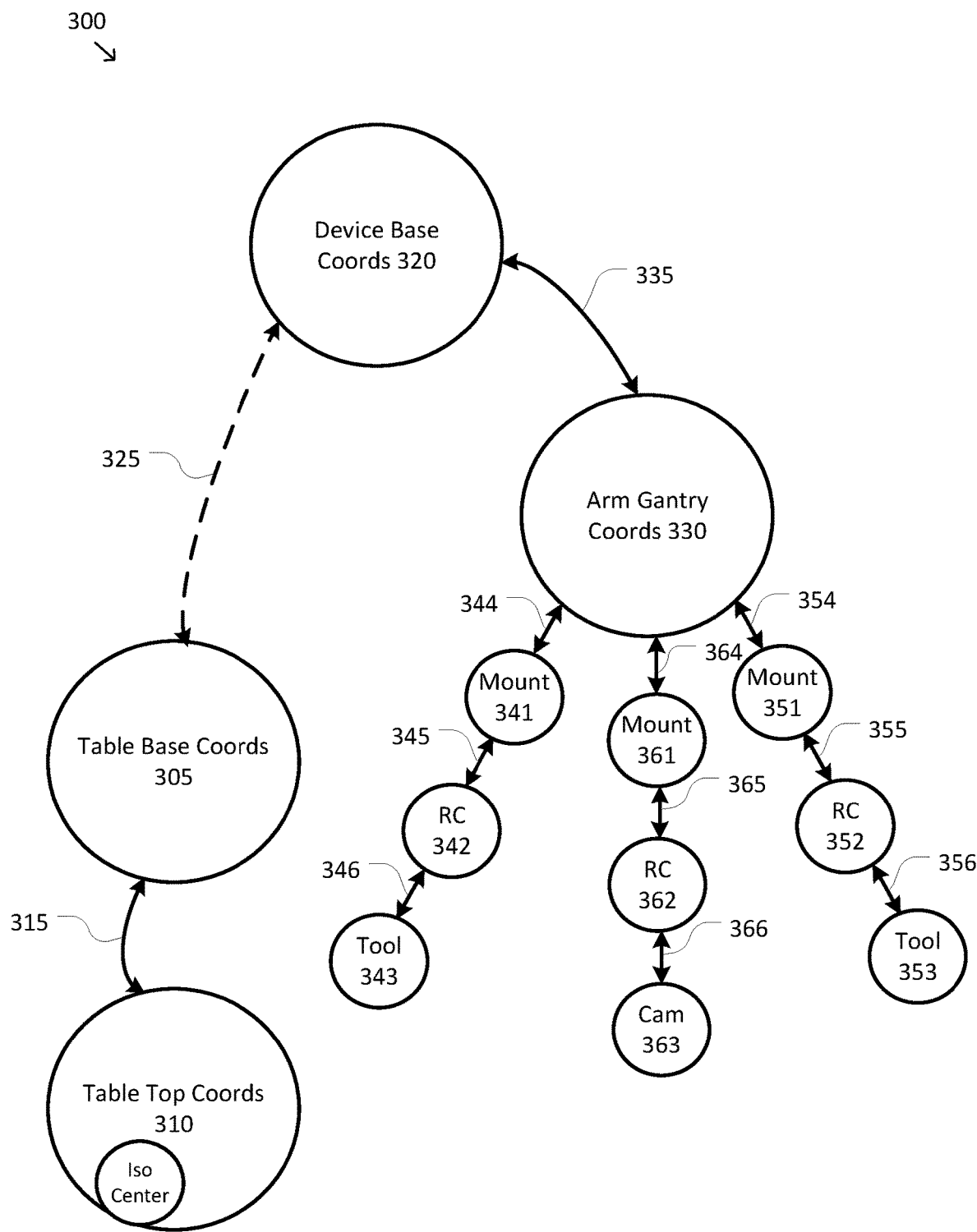
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. The kinematic information may be based on known kinematic models for the links and joints of a computer-assisted medical device and a surgical table. The kinematic information may be further based on information associated with the position and/or orientation of the joints of the computer-assisted medical device and the surgical table. In some examples, the information associated with the position and/or orientation of the joints may be derived from one or more sensors, such as encoders, measuring the linear positions of prismatic joints and the rotational positions of revolute joints.

The kinematic model 300 includes several coordinate frames or coordinate systems and transformations, such as homogeneous transforms, for transforming positions and/or orientation from one of the coordinate frames to another of the coordinate frames. In some examples, the kinematic model 300 may be used to permit the forward and/or reverse mapping of positions and/or orientations in one of the coordinate frames in any other of the coordinate frames by composing the forward and/or reverse/inverse transforms noted by the transform linkages included in FIG. 3. In some examples, when the transforms are modeled as homogenous transforms in matrix form, the composing may be accomplished using matrix multiplication. In some embodiments, the kinematic model 300 may be used to model the kinematic relationships of the computer-assisted device 210 and the surgical table 280 of FIG. 2.

The kinematic model 300 includes a table base coordinate frame 305 that may be used to model a position and/or orientation of a surgical table, such as surgical table 170 and/or surgical table 280. In some examples, the table base coordinate frame 305 may be used to model other points on the surgical table relative to a reference point and/or orientation associated with the surgical table. In some examples, the reference point and/or orientation may be associated with a table base of the surgical table, such as the table base 282. In some examples, the table base coordinate frame 305 may be suitable for use as a world coordinate frame for the computer-assisted system.

The kinematic model 300 further includes a table top coordinate frame 310 that may be used to model positions and/or orientations in a coordinate frame representative of a table top of the surgical table, such as the table top 284. In some examples, the table top coordinate frame 310 may be centered about a rotational center or iso center of the table top, such as iso center 286. In some examples, the z-axis of the table top coordinate frame 310 may be oriented vertically with respect to a floor or surface on which the surgical table is placed and/or orthogonal to the surface of the table top. In some examples, the x- and y-axes of the table top coordinate frame 310 may be oriented to capture the longitudinal (head to toe) and lateral (side-to-side) major axes of the table top. In some examples, a table base to table top coordinate transform 315 may be used to map positions and/or orientations between the table top coordinate frame 310 and the table base coordinate frame 305. In some examples, one or more kinematic models of an articulated structure of the surgical table, such as articulated structure 290, along with past and/or current joint sensor readings may be used to determine the table base to table top coordinate transform 315. In some examples consistent with the embodiments of FIG. 2, the table base to table top coordinate transform 315 may model the composite effect of the height, tilt, Trendelenburg, and/or slide settings associated with the surgical table.

The kinematic model 300 further includes a device base coordinate frame that may be used to model a position and/or orientation of a computer-assisted device, such as computer-assisted device 110 and/or computer-assisted device 210. In some examples, the device base coordinate frame 320 may be used to model other points on the computer-assisted device relative to a reference point and/or orientation associated with the computer-assisted device. In some examples, the reference point and/or orientation may be associated with a device base of the computer-assisted device, such as the mobile cart 215. In some examples, the device base coordinate frame 320 may be suitable for use as the world coordinate frame for the computer-assisted system.

In order to track positional and/or orientational relationships between the surgical table and the computer-assisted device, it may be desirable to perform a registration between the surgical table and the computer-assisted device. As shown in FIG. 3, the registration may be used to determine a registration transform 325 between the table top coordinate frame 310 and the device base coordinate from 320. In some embodiments, the registration transform 325 may be a partial or full transform between the table top coordinate frame 310 and the device base coordinate frame 320. In some examples, because the table base and the device base are typically located on the same level floor surface, the registration transform 325 may model just the rotational relationship of the device base to the table base about the z-axis of the table base coordinate frame 305 (e.g., a $\theta_Z$ registration). In some examples, the registration transform 325 may also model a horizontal offset between the table base coordinate frame 305 and the device base coordinate frame 320 (e.g., a XY registration). This is possible because the computer-assisted device and the surgical table are both positioned on the same horizontal ground plane (the floor) and operated in an upright position. In this operational relationship, height adjustments in the table base to table top transform 315 are analogous to vertical adjustments in the device base coordinate frame 320 because the vertical axes in the table base coordinate frame 305 and the device base coordinate frame 320 are the same or nearly the same so that height differences between the table base coordinate frame 305 and the device base coordinate frame 320 are within a reasonable tolerance of each other. In some examples, the tilt and Trendelenburg adjustments in the table base to table top transform 315 may be mapped to the device base coordinate frame 320 by knowing the height of the table top (or its iso center) and the $\theta_Z$ and/or XY registration. In some examples, the registration transform 325 and the table base to table top transform 315 may be used to model the computer-assisted surgical device as if it were attached to the table top.

The kinematic model 300 further includes an arm gantry coordinate frame 330 that may be used as a suitable model for a shared coordinate frame associated with the most proximal points on the articulated arms of the computer-assisted device. In some embodiments, the arm gantry coordinate frame 330 may be associated with and oriented relative to a convenient point on an arm gantry, such as the orientation platform 227. In some examples, the center point of the arm gantry coordinate frame 330 may be located on the axis 236 with the z-axis aligned with axis 236. In some examples, a device base to arm gantry coordinate transform 335 may be used to map positions and/or orientations between the device base coordinate frame 320 and the arm gantry coordinate frame 330. In some examples, one or more kinematic models of the links and joints of the computer-assisted device between the device base and the arm gantry, such as the set-up structure 220, along with past and/or current joint sensor readings may be used to determine the device base to arm gantry coordinate transform 335. In some examples consistent with the embodiments of FIG. 2, the device base to arm gantry coordinate transform 335 may model the composite effect of the two-part column, shoulder joint, two-part boom, and wrist joint of the computer-assisted device.

The kinematic model 300 further includes a series of coordinate frames and transforms associated with each of the articulated arms of the computer-assisted device. As shown in FIG. 3, the kinematic model 300 includes coordinate frames and transforms for three articulated arms, although one of ordinary skill would understand that different computer-assisted devices may include fewer and/or more articulated arms. Consistent with the configuration of the links and joints of the computer-assisted device 210 of FIG. 2, each of the articulated arms may be modeled using a manipulator mount coordinate frame, a remote center coordinate frame, and a tool or camera coordinate frame, depending on a type of instrument mounted to the distal end of the articulated arm.

In the kinematic model 300, the kinematic relationships of a first one of the articulated arms is captured using a manipulator mount coordinate frame 341, a remote center coordinate frame 342, a tool coordinate frame 343, a gantry to mount transform 344, a mount to remote center transform 345, and a remote center to tool transform 346. The manipulator mount coordinate frame 341 represents a suitable model for representing positions and/or orientations associated with a manipulator, such as manipulator 260. The manipulator mount coordinate frame 341 is typically associated with a manipulator mount, such as the manipulator mount 262 of the corresponding articulated arm. The gantry to mount transform 344 is then based on one or more kinematic models of the links and joints of the computer-assisted device between the arm gantry and the corresponding manipulator mount, such as the corresponding set-up joints 240, along with past and/or current joint sensor readings of the corresponding set-up joints 240.

The remote center coordinate frame 342 is typically associated with a remote center of the manipulator mounted on the articulated arm, such as the corresponding remote center 274 of the corresponding manipulator 260. The mount to remote center transform 345 is then based on one or more kinematic models of the links and joints of the computer-assisted device between the corresponding manipulator mount and the corresponding remote center, such as the corresponding joints 264, corresponding links 266, and corresponding carriage 268 of the corresponding manipulator 260, along with past and/or current joint sensor readings of the corresponding joints 264. When the corresponding remote center is being maintained in fixed positional relationship to the corresponding manipulator mounts, such as in the embodiments of FIG. 2, the mount to remote center transform 345 may include an essentially static translational component and a dynamic rotational component.

The tool coordinate frame 343 is typically associated with a tool and/or tool tip on an instrument mounted on the articulated arm, such as the corresponding tool 270 and/or tool tip 276. The remote center to tool transform 346 is then based on one or more kinematic models of the links and joints of the computer-assisted device that move and/or orient the corresponding tool and the corresponding remote center, along with past and/or current joint sensor readings. In some examples, the remote center to tool transform 346 accounts for the orientation at which the shaft, such as the corresponding shaft 272, passes through the remote center and the distance to which the shaft is advanced and/or retreated relative to the remote center. In some examples, the remote center to tool transform 346 may be constrained to reflect that the insertion axis of the shaft of the tool passes through the remote center and may account for rotations of the shaft and the tool tip about the axis defined by the shaft.

In the kinematic model 300, the kinematic relationships of a second one of the articulated arms is captured using a manipulator mount coordinate frame 351, a remote center coordinate frame 352, a tool coordinate frame 353, a gantry to mount transform 354, a mount to remote center transform 355, and a remote center to tool transform 356. The manipulator mount coordinate frame 351 represents a suitable model for representing positions and/or orientations associated with a manipulator, such as manipulator 260. The manipulator mount coordinate frame 351 is typically associated with a manipulator mount, such as the manipulator mount 262 of the corresponding articulated arm. The gantry to mount transform 354 is then based on one or more kinematic models of the links and joints of the computer-assisted device between the arm gantry and the corresponding manipulator mount, such as the corresponding set-up joints 240, along with past and/or current joint sensor readings of the corresponding set-up joints 240.

The remote center coordinate frame 352 is typically associated with a remote center of the manipulator mounted on the articulated arm, such as the corresponding remote center 274 of the corresponding manipulator 260. The mount to remote center transform 355 is then based on one or more kinematic models of the links and joints of the computer-assisted device between the corresponding manipulator mount and the corresponding remote center, such as the corresponding joints 264, corresponding links 266, and corresponding carriage 268 of the corresponding manipulator 260, along with past and/or current joint sensor readings of the corresponding joints 264. When the corresponding remote center is being maintained in fixed positional relationship to the corresponding manipulator mounts, such as in the embodiments of FIG. 2, the mount to remote center transform 355 may include an essentially static translational component and a dynamic rotational component.

The tool coordinate frame 353 is typically associated with a tool and/or tool tip on an instrument mounted on the articulated arm, such as the corresponding tool 270 and/or tool tip 276. The remote center to tool transform 356 is then based on one or more kinematic models of the links and joints of the computer-assisted device that move and/or orient the corresponding tool and the corresponding remote center, along with past and/or current joint sensor readings. In some examples, the remote center to tool transform 356 accounts for the orientation at which the shaft, such as the corresponding shaft 272, passes through the remote center and the distance to which the shaft is advanced and/or retreated relative to the remote center. In some examples, the remote center to tool transform 356 may be constrained to reflect that the insertion axis of the shaft of the tool passes through the remote center and may account for rotations of the shaft and the tool tip about the insertion axis defined by the shaft.

In the kinematic model 300, the kinematic relationships of a third one of the articulated arms is captured using a manipulator mount coordinate frame 361, a remote center coordinate frame 362, a camera coordinate frame 363, a gantry to mount transform 364, a mount to remote center transform 365, and a remote center to camera transform 366. The manipulator mount coordinate frame 361 represents a suitable model for representing positions and/or orientations associated with a manipulator, such as manipulator 260. The manipulator mount coordinate frame 361 is typically associated with a manipulator mount, such as the manipulator mount 262 of the corresponding articulated arm. The gantry to mount transform 364 is then based on one or more kinematic models of the links and joints of the computer-assisted device between the arm gantry and the corresponding manipulator mount, such as the corresponding set-up joints 240, along with past and/or current joint sensor readings of the corresponding set-up joints 240.

The remote center coordinate frame 362 is typically associated with a remote center of the manipulator mounted on the articulated arm, such as the corresponding remote center 274 of the corresponding manipulator 260. The mount to remote center transform 365 is then based on one or more kinematic models of the links and joints of the computer-assisted device between the corresponding manipulator mount and the corresponding remote center, such as the corresponding joints 264, corresponding links 266, and corresponding carriage 268 of the corresponding manipulator 260, along with past and/or current joint sensor readings of the corresponding joints 264. When the corresponding remote center is being maintained in fixed positional relationship to the corresponding manipulator mounts, such as in the embodiments of FIG. 2, the mount to remote center transform 365 may include an essentially static translational component and a dynamic rotational component.

The camera coordinate frame 363 is typically associated with an imaging device, such an endoscope, mounted on the articulated arm. The remote center to camera transform 366 is then based on one or more kinematic models of the links and joints of the computer-assisted device that move and/or orient the imaging device and the corresponding remote center, along with past and/or current joint sensor readings. In some examples, the remote center to camera transform 366 accounts for the orientation at which the shaft, such as the corresponding shaft 272, passes through the remote center and the distance to which the shaft is advanced and/or retreated relative to the remote center. In some examples, the remote center to camera transform 366 may be constrained to reflect that the insertion axis of the shaft of the imaging device passes through the remote center and may account for rotations of the imaging device about the axis defined by the shaft.

As discussed above and further emphasized here, FIG. 3 is merely an example which should not unduly limit the scope of the claims. One of ordinary skill in the art would recognize many variations, alternatives, and modifications. According to some embodiments, the registration between the surgical table and the computer-assisted device may be determined between the table top coordinate frame 310 and the device base coordinate frame 320 using an alternative registration transform. When the alternative registration transform is used, registration transform 325 may be determined by composing the alternative registration transform with the inverse/reverse of the table base to table top transform 315. According to some embodiments, the coordinate frames and/or transforms used to model the computer-assisted device may be arranged differently dependent on the particular configuration of the links and joints of the computer-assisted device, its articulated arms, its end effectors, its manipulators, and/or its instruments. According to some embodiments, the coordinate frames and transforms of the kinematic model 300 may be used to model coordinate frames and transforms associated with one or more virtual tools and/or virtual cameras. In some examples, the virtual tools and/or cameras may be associated with previously stored and/or latched tool positions, projections of tools and/or cameras due to a motion, reference points defined by a surgeon and/or other personnel, and/or the like.

As described previously, as a computer-assisted system, such as computer-assisted systems 110 and/or 210, is being operated it would be desirable to allow continued control of the tool and/or tool tips while motion of a surgical table, such as surgical tables 170 and/or 280, is allowed. In some examples, this may allow for a less time-consuming procedure as surgical table motion may occur without having to undock the manipulators from the patient. In some examples, this may allow a surgeon and/or other medical personnel to monitor organ movement while the surgical table motion is occurring to obtain a more optimal surgical table pose. In some examples, this may also permit active continuation of a surgical procedure during surgical table motion.

As a computer-assisted system, such as computer-assisted systems 110 and/or 200 are being operated, one of the goals is to maintain an appropriate pose for each of the tools and/or tool tips. In one mode of operation for the computer-assisted system, the joints of the surgical table and the joints proximal to each of the manipulators are locked and/or held in place through the use of servo controls and/or brakes so that motion of the joints is limited and/or prohibited entirely. This allows the joints of the manipulators to control the pose of the tools to accomplish a desired procedure without interference from movement in these other joints. In some examples, the manipulators may be docked with a patient during the procedure. In some examples, the pose of the tools and/or tool tips may be controlled via teleoperation by a surgeon at an operator console. It may, however, be desirable to support other modes of operation for the computer-assisted system that allow for movement in the articulated arms while the tools remain docked to the patient. These other modes of operation may introduce risks that are not present in modes of operation when the tools are not docked to the patient. In some examples, these risks may include injury to the patient when the tools and/or tool tips are allowed to move relative to the patient, breach of a sterile field, collisions between the articulated arms, and/or the like.

In a general case, these other modes of operation may be characterized by a goal of maintaining a pose of a tool, which is attached to a docked manipulator, relative to a patient when one or more joints proximal to the tool are subject to a disturbance that results in a change to positions and/or orientations (i.e., movements) of the one or more joints. Because disturbances in one or more first or disturbed joints proximal to a tool results in a change in the pose of the tool and its tool tip, it may be desirable to introduce movement in one or more second or compensating joints that compensate for the changes in the pose of the tool caused by the movement of the disturbed joints. Determining the extent of the disturbance and the amount of compensation depends on the type and nature of the disturbance, such as whether the disturbance is associated with movement of the surgical table or patient, or whether the disturbance is confined to the articulated arm used to manipulate the tool.

The disturbances associated with these other modes of operation that maintain a pose of a tool may be classified into two general categories. In the first category, the patient to which the manipulator is docked is not moving so that the pose of the tool and/or the tool tip may be monitored and maintained in any suitable world coordinate frame. The first category may include disturbances associated with controlled motion of the articulated arm. In some examples, the controlled motion of the articulated arm may include movement in one or more joints used to set-up the articulated arm and/or the manipulator before performing a procedure. One example of this includes the movement of one or more joints of the set-up structure of a computer-assisted device consistent with the embodiments of FIG. 2 where the orientation platform 227 is translated and aligned to allow the set-up joints 240 be moved to provide good range of motion in the manipulator 260 during a procedure. Examples of this type of motion are described in greater detail in U.S. Provisional Patent Application No. 62/024,887 entitled "System and Method for Aligning with a Reference Target," which was filed on Jul. 15, 2014 and U.S. Provisional Patent Application No. 61/954,261 entitled "System and Method for Aligning with a Reference Target," which was filed on Mar. 17, 2014, both of which are hereby incorporated by reference. Another example of this includes movement of one or more joints to provide collision avoidance with another articulated arm and/or known obstacle in proximity to the articulated arm. The first category may further include disturbances associated with the release of brakes and/or other joint locks prior to initiating other motion. In some examples, external forces and/or torques on the shaft of the tool, such as due to forces and torques applied to the remote center of the manipulator by the body wall of the patient, may result in undesirable motion of the tool and/or the tool tip when the brakes and/or locks are released and forces and/or torques are absorbed by the released joints. The first category may further include disturbances caused by operation of the articulated arm in a clutched or float state such as might occur during manual repositioning of the articulated arm by an operator and/or due to a collision between the articulated arm and an obstacle. Examples of this type of motion are described in greater detail in U.S. Provisional Patent Application No. 61/954,120 entitled "System and Method for Breakaway Clutching in an Articulated Arm," which was filed on Mar. 17, 2014 and which is hereby incorporated by reference.

In the second category, the patient to whom the manipulator is docked is moving so that the pose of the tool and/or the tool tip may be monitored in a local coordinate frame. The second category may include disturbances caused by allowing motion of the articulated structure in the surgical table (i.e., table movement) or movement of the patient relative to the surgical table. In the second category, it is generally desired to have the articulated arm and the tool move with the patient so that the pose of the tool relative to the patient does not change. In some examples, this may be accomplished using port dragging that may include releasing and/or unlocking one or more joints of the articulated arm and allowing the body wall of the patient at the port to drag the remote center and the tool as the patient moves. In some examples, as the remote center moves the orientation of the tool relative to the remote center may begin to change resulting in a change between the pose of tool relative to the patient.

Figure 4:
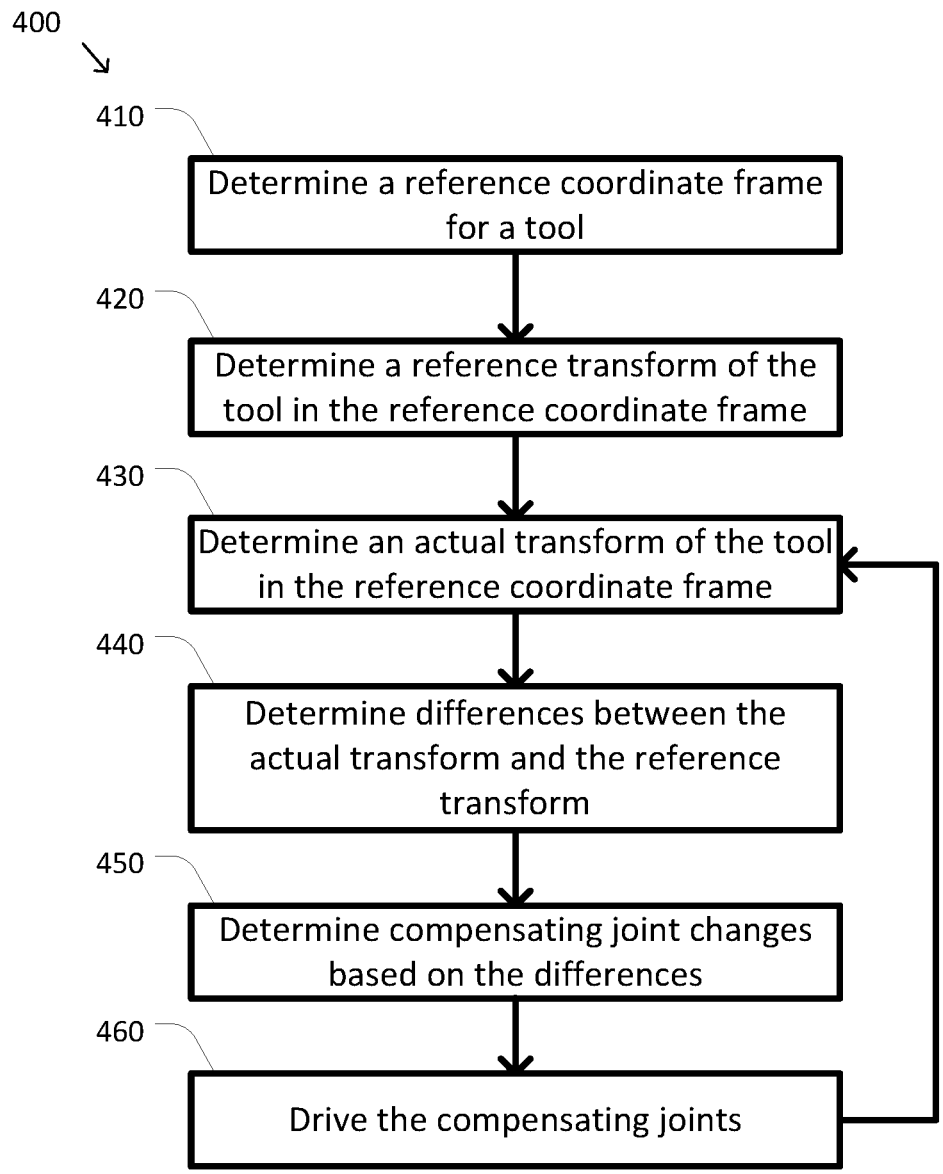
FIG. 4 is a simplified diagram of the method of maintaining the pose of a tool during movement of one or more joints proximal to the tool according to some embodiments.

FIG. 4 is a simplified diagram of the method 400 of maintaining the pose of a tool during movement of one or more joints proximal to the tool according to some embodiments. One or more of the processes 410-460 of method 400 may be implemented, at least in part, in the form of executable code stored on non-transient, tangible, machine readable media that when run by one or more processors (e.g., the processor 140 in control unit 130) may cause the one or more processors to perform one or more of the processes 410-460. In some embodiments, method 400 may be used to compensate for changes in the pose of the tool due to motion in one or more disturbed joints by introducing compensating motion in one or more compensating joints. In some examples, method 400 may be used when the motion in the disturbed joints is due to controlled motion, clutched motion, brake or lock release, patient motion, and/or the like. In some examples consistent with the embodiments of FIG. 2, the one or more disturbed joints and/or the one or more compensating joints may include any of the joints in set-up structure 220, the set-up joints 240, and/or any joints of manipulator 260 proximal to the tool. In some embodiments, use of method 400 may be limited to operation when an instrument, cannula, and/or the like is coupled to the distal end of a corresponding articulated arm, end effector, and/or manipulator so that a remote center for the articulated arm, end effector, and/or manipulator may be defined. In some embodiments, method 400 may include having the pose of the tool at least partially maintained using resistance from a patient port and/or by an operator of the computer-assisted device.

According to some embodiments, method 400 may support one or more useful improvements over methods that do not maintain the pose of the tool during movement of the one or more disturbed joints. In some examples, method 400 may reduce the likelihood of collisions between the tool and/or other links and joints of the articulated arm to which the tool is mounted and other articulated arms, end effectors, manipulators, and/or tools whose positions and orientations are known to the computer-assisted device. In some examples, method 400 may reduce the movement of one or more sterile drapes attached to the articulated arm to which the tool is mounted so as to better avoid sweeping and/or moving the one or more sterile drapes into contact with one or more non-sterile obstacles, such as one or more exposed regions of an operator (e.g., the operator's face) and the resultant breach of a sterile field. In some examples, method 400 may reduce the likelihood of moving and/or sweeping the tool and/or the tool tip within the body of the patient so as to reduce the likelihood of injury to the patient by the tool and/or the tool tip.

At a process 410, a reference coordinate frame for a tool is determined. The determination of the reference coordinate frame for the tool depends on an operating mode. In some examples, the determination of the reference frame may further depend on a type of disturbance expected for the articulated arm to which the tool is mounted and/or the one or more joints (i.e., the disturbed joints) that may move as a result of the disturbance. When the source of the disturbance is associated with a controlled motion of the articulated arm, manual repositioning of the articulated arm, motion induced by a collision of the articulated arm, and/or the like where the patient is not moving and the remote center for the manipulator mounted to the articulated arm is not subject to translation, any coordinate frame that is fixed relative to a world coordinate frame may be used. Consistent with the embodiments of FIGS. 2 and 3, any of the device base coordinate frame 320, arm gantry coordinate frame 330, and/or remote center coordinate frames 342, 352, and 362 may be used as the reference coordinate frame. When the source of the disturbance is associated with brake and/or lock release of one or more of the disturbed joints such that the remote center may move, any coordinate frame that is fixed relative to a world coordinate frame may be used. Consistent with the embodiments of FIGS. 2 and 3, any of the device base coordinate frame 320 and/or arm gantry coordinate frame 330, but not any of the remote center coordinate frames 342, 352, and 362, may be used as the reference coordinate frame. When the source of the disturbance is associated with patient motion and/or movement of the surgical table, a local coordinate frame that moves with the patient may be used. Consistent with the embodiments of FIGS. 2 and 3, the remote center coordinate frame 342, 352, or 362 associated with the articulated arm and/or table top coordinate frame 310 may be used as the reference coordinate frame.

At a process 420, a reference transform of the tool in the reference coordinate frame is determined. Prior to the initiation of movement of the one or more disturbed joints, one or more kinematic models of the computer-assisted device are used to determine a reference transform for the tool in the reference coordinate frame determined during process 410. In some examples, the one or more kinematic models may include one or more kinematic models for the links and joints of the articulated arm, the manipulator, the tool, the set-up structure and/or the like. Using the embodiments of FIGS. 2 and 3 as an example, when the reference coordinate frame is the remote center coordinate frame 342, 352, or 362, the respective remote center to tool/camera transform 346, 356, or 366 latched or recorded before the disturbance begins becomes the reference transform of the tool. When the reference coordinate frame is the arm gantry coordinate frame 330, a composition of the corresponding gantry to mount transform 344, 354, or 364, the corresponding mount to remote center transform 345, 355, or 365, and the corresponding remote center to tool/camera transform 346, 356, or 366 latched or recorded before the disturbance begins becomes the reference transform of the tool. In some examples, when a tool is not mounted to the articulated arm, end effector, and/or manipulator, a cannula and/or a virtual tool may be used to determine the reference transform based on the insertion direction of the cannula and/or a virtual shaft of the instrument.

At a process 430, an actual transform of the tool in the reference coordinate frame is determined. As the one or more disturbed joints begin to move due to the disturbance, the pose of the tool begins to change because the tool is distal to the one or more disturbed joints. The movement of the one or more disturbed joints is monitored and the same one or more kinematic models used during process 420 are again applied using current joint positions and/or orientations to determine the actual transform of the tool in the reference coordinate frame. The actual transform represents how the movements of the one or more disturbed joints are tending to move the tool away from the pose that is to be maintained.

At a process 440, differences between the actual transform and the reference transform are determined. The differences between the actual transform and the reference transform represent errors that are being introduced into the pose of the tool by the disturbance. Unless the errors in the pose of the tool are compensated for by movement using one or more compensating joints of the articulate arm, the pose of the tool may undesirably change. In some examples, the differences may be determined by subtracting corresponding matrix and/or vector representations of the actual and reference transforms. In some examples, the differences may be represented as an error transform determined by composing an inverse/reverse of the reference transform with the actual transform.

At a process 450, compensating joint changes are determined based on the differences. Using the differences between the actual transform and the reference transform determined during process 440, changes in the one or more compensating joints are determined. The differences between the actual transform and the reference transform are mapped from the reference coordinate system of the actual and reference transforms to one or more local coordinate systems associated with each of the compensating joints. In effect, this transforms the errors in the pose of the tool from the reference coordinate system to errors of the pose relative to the compensating joints. In some examples, one or more kinematic models may be used to transform the differences to the local coordinate systems. In some examples, the compensating joints may include any of the joints of the articulated arm and/or the manipulator that are not one of the disturbed joints. Once the relative errors in the pose are determined, they may be used to determine the movements for each of the compensating joints. In some examples, an inverse Jacobian may be used to map the relative errors to compensating movements of the compensating joints. In some examples, the movements in the compensating joints may be applied as joint velocities applied to the compensating joints.

At a process 460, the compensating joints are driven. One or more commands are sent to the one or more actuators in the compensating joints based on the movements of the compensating joints determined during process 450. The commands sent to the compensating joints correct for the errors in the pose of the tool introduced by the movements in the one or more disturbed joints so that the pose of the tool in the reference coordinate system is maintained with minimal error. As long as the one or more compensating joints continue to make corrective changes to the pose of the tool, processes 430-460 are repeated to compensate for any errors introduced into the pose of the tool.

According to some embodiments, process 460 may be subject to practical limitations. In some examples, the ability of one or more of the compensating joints to compensate for the errors in the pose of the tool may be limited by range of motion (ROM) limits of the one or more compensating joints. In some examples, when a ROM limit for one or more of the compensating joints is reached and/or is about to be reached method 400 and/or process 460 may be stopped and an error may be indicated to the operator using one or more visible and/or audible error cues. In some examples, rather than stopping operation of method 400 and/or process 460, process 460 may operate in modified form to partially compensate for the errors in the pose of the tool so as to minimize the controllable error while providing feedback to the operator that not all of the movement caused by the disturbance is being compensated for. In some examples, the feedback may include one or more visible and/or audio cues indicating that compensation is limited and/or the application of resistance on the one or more compensating joints. In some examples, the resistance may include partially applying one or more brakes associated with the one or more compensating joints and/or applying a motion resistance voltage and/or signal in one or more actuators associated with the one or more compensating joints.

As discussed above and further emphasized here, FIG. 4 is merely an example which should not unduly limit the scope of the claims. One of ordinary skill in the art would recognize many variations, alternatives, and modifications. According to some embodiments, method 400 may be independently applied for each of the tools being manipulated by the computer-assisted device. In some examples, the tools may include any of the tools docked to the patient. In some examples, the compensating joints may be located distal to an arm gantry, such as orientation platform 227, of the computer-assisted device so that compensation to maintain the pose of each of the tools is applied separately for each of the tools.

According to some embodiments, the disturbed and compensating joints may not include each of the joints in the articulated arm and/or manipulator. In some examples, the compensating joints may include just the roll, pitch, and yaw joints of the manipulator. In some examples, other joints in the articulated arm and/or the manipulator may be locked to prevent their relative movement during method 400. In some examples, one or more non-actuated joints of the articulated arm and/or the manipulator may be unlocked and/or placed in a clutched and/or float state during method 400 so that errors in the pose of the tool may be at least partially reduced by changes in the unlocked joints. In some examples, the changes in the unlocked joints may reduce the amount that the compensating joints are to be driven. In some examples, the pose of the tool may be at least partially maintained using resistance from the patient port and/or by an operator of the computer-assisted device.

According to some embodiments, one or more of the processes 430-460 may be performed concurrently. According to some embodiments, additional conditions may result in premature termination of method 400 such as by returning control of the computer-assisted device to an operator and/or by suspension of operation of the computer-assisted device. In some examples, the additional conditions may include inability to complete the compensated movement, manual intervention and/or override from an operator using one or more controls on an operator workstation and/or the articulated arms, detection of operator disengagement with the operator workstation using one or more safety interlocks, position tracking errors in the computer-assisted device, system faults, and/or the like. In some examples, the desired movement may not be possible due to the detection of imminent collisions among the links and/or joints of the computer-assisted device, range of motion limits in one or more of the joints of the computer-assisted device, inability to maintain the pose of the tool due to motion of the patient, and/or the like. In some examples, premature termination of method 400 may result in an error notification being sent to the operator. In some examples, the error notification may include any visual and/or audible indicator, such as a text message, a blinking light, an audible tone, a spoken phrase, and/or the like.

Some examples of control units, such as control unit 130 may include non-transient, tangible, machine readable media that include executable code that when run by one or more processors (e.g., processor 140) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device, the device comprising:
an articulated structure comprising a plurality of joints; and
a control unit coupled to the articulated structure;
wherein the control unit is configured to:
determine whether a cannula or an instrument is coupled to a distal end of the articulated structure; and
in response to determining that the cannula or the instrument is coupled to the distal end of the articulated structure:
determine an initial position and orientation of the instrument prior to detection of a disturbance in a first joint of the plurality of joints;
determine, during the disturbance in the first joint, a current position and orientation of the instrument;
determine a difference between the current position and orientation and the initial position and orientation; and
drive at least a second joint of the plurality of joints based on the difference.

2. The device of claim 1, wherein the articulated structure is configured to be coupled to a patient, and the initial position and orientation and the current position and orientation are determined relative to a reference coordinate frame associated with a top of a table on which the patient is positioned.

3. The device of claim 1, wherein the driving of the at least second joint maintains a position and orientation of the instrument at the initial position and orientation.

4. The device of claim 1, wherein the driving of the at least second joint partially reduces the difference between the current position and orientation and the initial position and orientation.

5. The device of claim 1, wherein the disturbance in the first joint causes movement of the first joint.

6. The device of claim 1, wherein when the disturbance in the first joint is due to movement of a patient coupled to the articulated structure, the initial position and orientation of the instrument and the current position and orientation are determined relative to a reference coordinate frame associated with a remote center of the articulated structure.

7. The device of claim 1, wherein when the disturbance in the first joint is due to controlled motion of the articulated structure, due to manual repositioning of the articulated structure, due to motion induced by a collision, or due to release of a brake or lock of the first joint, the initial position and orientation of the instrument and the current position and orientation are determined relative to a reference coordinate frame fixed relative to a world coordinate frame of the computer-assisted device.

8. The device of claim 1, wherein the first joint is a non-actuated joint.

9. The device of claim 1, wherein in response to determining that the second joint is at a range of motion limit, the control unit is further configured to stop driving the second joint based on the difference between the current position and orientation and the initial position and orientation.

10. The device of claim 1, wherein the control unit is further configured to unlock a third joint of the plurality of joints, wherein unlocking the third joint reduces an amount the second joint is driven based on the difference between the current position and orientation and the initial position and orientation.

11. A method of compensating for motion in a computer-assisted device comprising an articulated structure, the method comprising:
determining whether a cannula or an instrument is coupled to a distal end of the articulated structure; and
in response to determining that the cannula or the instrument is coupled to the distal end of the articulated structure:
determining an initial position and orientation of the instrument prior to detection of a disturbance in a first joint of a plurality of joints of the articulated structure;
determining, during the disturbance in the first joint, a current position and orientation of the instrument;
determining a difference between the current position and orientation and the initial position and orientation; and
driving at least a second joint of the plurality of joints based on the difference.

12. The method of claim 11, wherein the articulated structure is configured to be coupled to a patient, and the initial position and orientation and the current position and orientation are determined relative to a reference coordinate frame associated with a top of a table on which the patient is positioned.

13. The method of claim 11, wherein the driving of the at least second joint maintains a position and orientation of the instrument at the initial position and orientation.

14. The method of claim 11, wherein the driving of the at least second joint partially reduces the difference between the current position and orientation and the initial position and orientation.

15. The method of claim 11, wherein the initial position and orientation of the instrument and the current position and orientation of the instrument are determined relative to a reference coordinate frame determined based on a cause of the disturbance in the second joint.

16. The method of claim 11, further comprising: stopping the driving of the second joint in response to determining that the second joint is at a range of motion limit.

17. A non-transitory machine-readable medium comprising a plurality of machine-readable instructions which when executed by one or more processors associated with a device comprising an articulated structure are adapted to cause the one or more processors to perform a method comprising:
determining whether a cannula or instrument is coupled to a distal end of the articulated structure; and
in response to determining that the cannula or the instrument is coupled to the distal end of the articulated structure:
determining an initial position and orientation of the instrument prior to detection of a disturbance in a first joint of a plurality of joints of the articulated structure;

determining, during the disturbance in the first joint, a current position and orientation of the instrument;

determining a difference between the current position and orientation and the initial position and orientation; and driving at least a second joint of the plurality of joints based on the difference.

18. The non-transitory machine-readable medium of claim 17, wherein the driving of the at least second joint maintains a position and orientation of the instrument at the initial position and orientation.

19. The non-transitory machine-readable medium of claim 17, wherein the driving of the at least second joint partially reduces the difference between the current position and orientation and the initial position and orientation.

20. The non-transitory machine-readable medium of claim 17, wherein the initial position and orientation of the instrument and the current position and orientation of the instrument are determined relative to a reference coordinate frame determined based on a cause of the disturbance in the second joint.

* * * * *

UNITED STATES PATENT AND TRADEMARK OFFICE
CERTIFICATE OF CORRECTION

PATENT NO. : 11,129,684 B2
APPLICATION NO. : 16/743218
DATED : September 28, 2021
INVENTOR(S) : Brandon D. Itkowitz et al.

It is certified that error appears in the above-identified patent and that said Letters Patent is hereby corrected as shown below:

On the Title Page

(63) Related U.S. Application Data:
Please delete "Continuation of application No. 16/101,328, filed on Aug. 10, 2018, now Pat. No. 10,575,910, which is a continuation of application No. 15/125,533, filed as application No. PCT/US2015/021089 on Mar. 17, 2015, now Pat. No. 10,070,931." and insert --Continuation of application No. 16/101,328, filed on Aug. 10, 2018, now Pat. No. 10,575,910, which is a continuation of application No. 15/125,533, filed on Sep. 12, 2016, now Pat. No. 10,070,931, which is a 371 of application No. PCT/US2015/021089, filed on Mar. 17, 2015.--.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*